(12) United States Patent
Ogino et al.

(10) Patent No.: US 11,100,638 B2
(45) Date of Patent: Aug. 24, 2021

(54) MEDICAL IMAGING DEVICE AND MEDICAL IMAGE PROCESSING METHOD USING A NEUTRAL NETWORK

(71) Applicant: Hitachi, Ltd., Tokyo (JP)

(72) Inventors: Masahiro Ogino, Tokyo (JP); Yoshimi Noguchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 27 days.

(21) Appl. No.: 16/630,594

(22) PCT Filed: Jun. 1, 2018

(86) PCT No.: PCT/JP2018/021200
§ 371 (c)(1),
(2) Date: Jan. 13, 2020

(87) PCT Pub. No.: WO2019/026407
PCT Pub. Date: Feb. 7, 2019

(65) Prior Publication Data
US 2020/0175675 A1 Jun. 4, 2020

(30) Foreign Application Priority Data
Jul. 31, 2017 (JP) .............................. JP2017-148198

(51) Int. Cl.
G06T 7/00 (2017.01)
G06T 5/00 (2006.01)
G01R 33/48 (2006.01)

(52) U.S. Cl.
CPC ........ *G06T 7/0012* (2013.01); *G01R 33/4818* (2013.01); *G06T 5/001* (2013.01);
(Continued)

(58) Field of Classification Search
CPC .................. G06T 7/0012; G06T 5/001; G06T 2207/10081; G06T 2207/10088;
(Continued)

(56) References Cited

U.S. PATENT DOCUMENTS

| 9,846,214 B2 | 12/2017 | Zhou et al. |
| 2016/0055627 A1 | 2/2016 | Shibata et al. |
| 2017/0003368 A1* | 1/2017 | Rathi ............... G01R 33/56341 |

FOREIGN PATENT DOCUMENTS

| JP | 2015-129987 A | 7/2015 |
| JP | 2016-123853 A | 7/2016 |
| JP | 2016-168293 A | 9/2016 |
| JP | 2017-45341 A | 3/2017 |
| WO | WO 2014/162690 A1 | 10/2014 |

OTHER PUBLICATIONS

Chao Dong, Chen Change Loy, Kaming He, and Xiaoou Tang: "Image Super-Resolution Using Deep Convolutional Networks", Jul. 31, 2015. (Year: 2015).*

(Continued)

*Primary Examiner* — Siamak Harandi
(74) *Attorney, Agent, or Firm* — Crowell & Moring LLP

(57) ABSTRACT

Provided is a medical imaging device capable of obtaining a medical image with high image quality in a short time by using a novel image reconstruction technique in which DL is applied to medical image processing and by significantly reducing a total imaging time including an image reconstruction time. The medical imaging device classifies a medical image into any of a predetermined plurality of classes, selects an optimal one or a plurality of restorers from a plurality of restorers respectively corresponding to the plurality of classes according to classification results, and reconstructs the medical image using the selected restorers. The medical image is divided into, for example, a plurality of patches, and is reconstructed for each patch and integrated. The restorer can include a CNN.

13 Claims, 17 Drawing Sheets

(52) U.S. Cl.
CPC .......... *G06T 2207/10081* (2013.01); *G06T 2207/10088* (2013.01); *G06T 2207/20081* (2013.01); *G06T 2207/20084* (2013.01); *G06T 2207/30004* (2013.01); *G06T 2207/30168* (2013.01)

(58) Field of Classification Search
CPC . G06T 2207/20081; G06T 2207/20084; G06T 2207/30004; G06T 2207/30168; G06T 11/008; G06T 11/003; G01R 33/4818; G01R 33/5608; A61B 5/00; A61B 5/055; A61B 6/03; A61B 8/14
See application file for complete search history.

(56) References Cited

OTHER PUBLICATIONS

International Search Report (PCT/ISA/210) issued in PCT Application No. PCT/JP2018/021200 dated Aug. 28, 2018 with English translation (five (5) pages).

Japanese-language Written Opinion (PCT/ISA/237) issued in PCT Application No. PCT/JP2018/021200 dated Aug. 28, 2018 (four (4) pages).

Ishida, "1. Development of image processing technique using AI," Innervision, Jul. 2017, pp. 24-27, vol. 32, No. 7 with partial English translation (four (4) pages).

Romano et al., "RAISR: Rapid and Accurate Image Super Resolution," arXiv.org, arXiv :1606.01299v3, 2016, https://arxiv.org/pdf/106.01299.pdf, (31 pages).

Inamuro et al., "High-Quality MR Imaging Based on Dictionary Learning Using Training Images and Observed Signals," IEICE technical report, Jan. 2017, pp. 123-128, vol. 116 with English language abstract and partial English translation (six (6) pages).

Dong et al., "Image Super-Resolution Using Deep Convolutional Networks," arXiv.org, arXiv :1501.00092v3, 2015, https://arxiv.org/pdf/1501.00092.pdf, (14 pages).

English translation of Ishida et al., "1. Development of image processing technique using AI," Innervision, Jul. 2017, pp. 24-27, vol. 32, No. 7 (five (5) pages) (previously submitted as C3).

International Preliminary Report on Patentability (PCT/IB/338 & PCT/IB/373) issued in PCT Application No. PCT/JP2018/021200 dated Feb. 13, 2020, including English translation of document C2 (Japanese-language Written Opinion (PCT/ISA/237) previously filed on Jan. 13, 2020 ( eight pages).

* cited by examiner

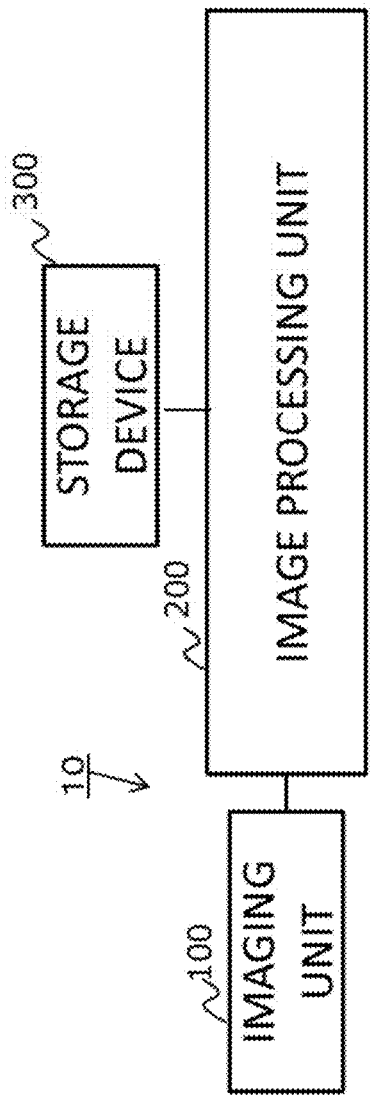
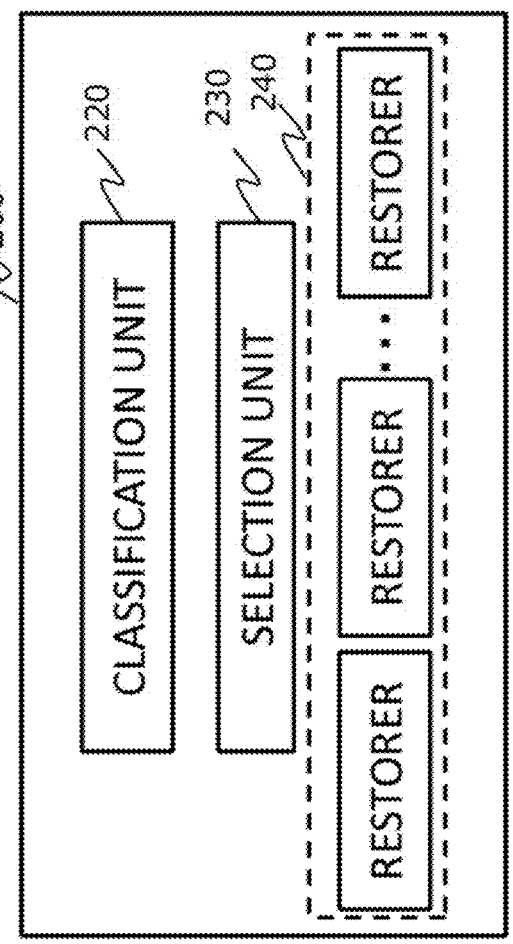

MEDICAL IMAGING DEVICE AND MEDICAL IMAGE PROCESSING METHOD USING A NEUTRAL NETWORK

TECHNICAL FIELD

The present invention relates to a medical imaging device such as a magnetic resonance imaging (hereinafter referred to as an MRI) device, a CT device, and an ultrasonic imaging device, and particularly to high-speed processing of image reconstruction combined with high-speed imaging.

BACKGROUND ART

In many medical imaging devices such as the MRI device, as an amount of data or signals obtained at the time of imaging increases, image quality of an image obtained by reconstruction from them is improved. However, since an increase in the amount of data to be obtained also leads to an increase in imaging time, a high-speed imaging method that reduces the imaging time without degrading the image quality by devising the imaging method has been developed in each modality. For example, in the MRI device, the high-speed imaging method (a parallel imaging) has been put into practical use in which the imaging time is reduced by undersampling k-space using a plurality of receiving coils, and the image is reconstructed by calculation using sensitivity distribution of the receiving coils.

An image reconstruction technique using compressed sensing (CS) has also been developed as one technique for reducing the imaging time. The CS is a technique for improving the image quality by performing repeat operation using sparsity on obtained sparse data. A technique in which the CS is applied to the medical imaging device is disclosed in, for example, Patent Literature 1.

Since the CS targets the sparse data, time required for data collection, that is, imaging can be reduced by applying this to the medical imaging device. However, CS calculation itself is the repeat operation and requires a certain amount of time to increase accuracy. Although it depends on performance of pulse sequence, CPU and the like, for example, a CS calculation time in double-speed imaging is about several times to 10 times an image reconstruction time using normal Fourier transform in the MRI device, and even if the imaging time is reduced by half, there is a limit to an effect of reducing an overall time from imaging start to image output.

Incidentally, in the field of image processing, deep learning (DL) is known as a technique for improving the accuracy of the image. The DL typically uses a convolutional neural network (CNN) that has been trained to classify images into multiple categories. Patent Literature 2 discloses a technique in which such DL is applied to a diagnostic device for diagnosing a skin disease from skin image data. In the technique, an ensemble discriminator is prepared by combining a plurality of discriminators (CNNs) corresponding to an original image and one or more converted images obtained by converting the original image, and a determination result is obtained by integrating discrimination values obtained by individual discriminators.

CITATION LIST

Patent Literature

Patent Literature 1: JP-A-2016-123853
Patent Literature 2: JP-A-2017-045341

SUMMARY OF THE INVENTION

Technical Problem

When applying DL to reconstruction of a medical image, it is necessary to construct a system different from disease determination and feature extraction as disclosed in Patent Literature 2. Further, a technique based on ensemble learning adopted in Patent Literature 2 is known to have a high predictive ability for unlearned data. However, for integration of results obtained by each discriminator, there is a problem in a method for determining weights during integration, and the like, and accuracy improvement of the image obtained by the integration is restricted.

An object of the present invention is to provide a novel image reconstruction technique using DL, and thereby to significantly reduce a total imaging time including the image reconstruction time and provide the medical image with high image quality.

Solution to Problem

In order to solve the above problems, the medical imaging device of the present invention classifies medical images into any of a predetermined plurality of classes, selects an optimal one or a plurality of restorers from a plurality of restorers respectively corresponding to the plurality of classes according to classification results, and performs the reconstruction process using the selected restorers. The medical image is divided into, for example, a plurality of patches (small areas), and is reconstructed for each patch and integrated. The restorer can include the CNN.

That is, the medical imaging device of the present invention includes: an imaging unit that collects image data from an inspection object; and an image processing unit that reconstructs an image using the image data collected by the imaging unit. The image processing unit includes: a classification unit that classifies the image data; an image restoring unit including a plurality of restorers corresponding to classifications by the classification unit; and a restorer selection unit that selects one or more restorers from the plurality of restorers according to classification results by the classification unit. Each of the plurality of restorers is a restorer including a neural network trained using learning data including a combination of a correct image and a degraded image for each classification, and restoring the image with high image quality from an input degraded image.

Advantageous Effects of the Invention

According to the present invention, it is possible to obtain a high-resolution image efficiently in a short time by classifying the image data prior to processing by the restorer, and processing the image data using the restorer selected from the plurality of restorers based on the classification results.

BRIEF DESCRIPTION OF THE DRAWINGS

FIGS. 1A and 1B are diagrams showing an outline of a medical imaging device of a first embodiment, FIG. 1A is a diagram showing an overall configuration of the device, and FIG. 1B is a diagram showing a configuration of an image processing unit.

DESCRIPTION OF EMBODIMENTS

The present invention can be applied to various medical imaging devices including an imaging unit and an image processing unit, such as an MRI device, a CT device, a PET (Positron Emission Tomography) device, and an ultrasonic imaging device. First, an embodiment having a configuration common to each modality will be described.

First Embodiment

As shown in (A) of FIG. 1, a medical imaging device 10 of the present embodiment includes an imaging unit 100 that collects data necessary for image reconstruction from a subject, and an image processing unit 200 that processes the data collected by the imaging unit 100 and generates an image. The medical imaging device 10 further includes a storage device 300 inside or outside thereof. The imaging unit 100 has a different configuration depending on the modality, but creates image data from signals obtained by measuring the subject. A detailed configuration for each modality will be described in an embodiment described below. The image data obtained by the imaging unit 100 is low spatial resolution data or undersampled data using, for example, a high-speed imaging method.

Figure 2:
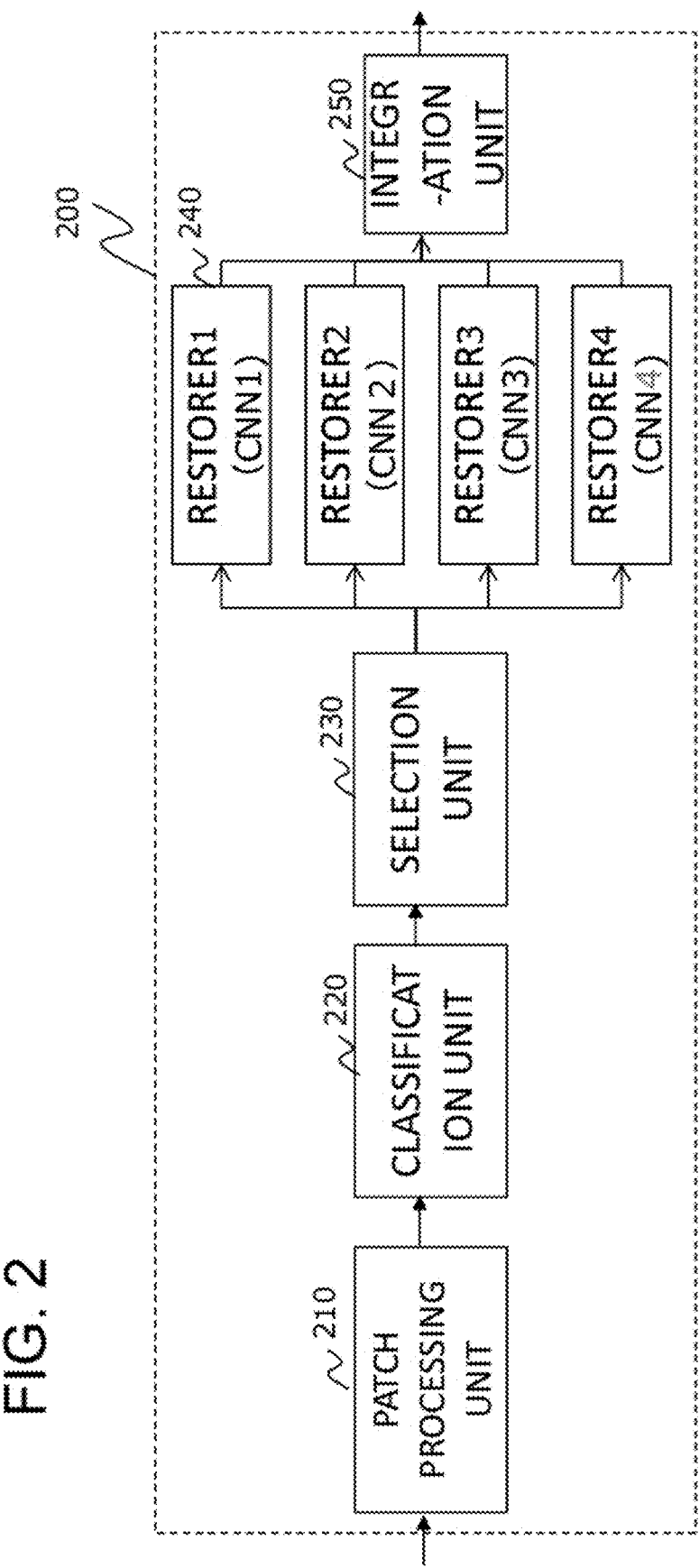
FIG. 2 is a diagram showing an operation flow of the image processing unit of the first embodiment.

As shown in (B) of FIG. 1, the image processing unit 200 includes an image restoring unit including a classification unit 220, a selection unit 230, and a plurality of restorers 240. The image processing unit 200 classifies the image data received from the imaging unit 100 into a plurality of clusters (classes) according to features of the image, selects a restorer 240 corresponding to the cluster into which the image data to be processed is classified from a plurality of restorers 240, and reconstructs the image by the selected restorer 240. When the image processing unit 200 divides the image data into image data patches and performs processing for each patch, as shown in FIG. 2, a patch processing unit 210 that cuts out the patches from the input image data, and an integration unit 250 that integrates the data after being processed by the restorer 240 for each patch are added to the image processing unit 200. The storage device 300 stores the data required for processing by the image processing unit 200. Specifically, a distribution diagram used by the classification unit 220 is stored. The distribution diagram is obtained by mapping results obtained by classifying a large number of image data for each feature in advance by the classification unit 220 to a space having the feature(s) as an axis (axes).

When the medical imaging device includes a CPU or a GPU as a calculation unit or a control unit, the image processing unit 200 has a function implemented as software installed in the CPU or the GPU. In particular, the restorer 240 included in the image processing unit 200 is implemented by a neural network having a learning function, and a known software package such as a CNN can be used. Some functions of the image processing unit 200 can also be implemented by hardware such as an ASIC (Application Specific Integrated Circuit) or an FPGA (Field Programmable Gate Array).

Hereinafter, an operation of the image processing unit 200 will be described using an example of processing for each patch. First, prior to description of procedures for the image processing unit 200 to process the image captured by the imaging unit 100, the distribution diagram and learning data stored in the storage device 300 and learning by the restorer 240 will be described.

The learning data is data for the classification unit 220 to classify the image data received from the imaging unit 100 or the patches cut out therefrom, and is generated as follows.

Figure 3:
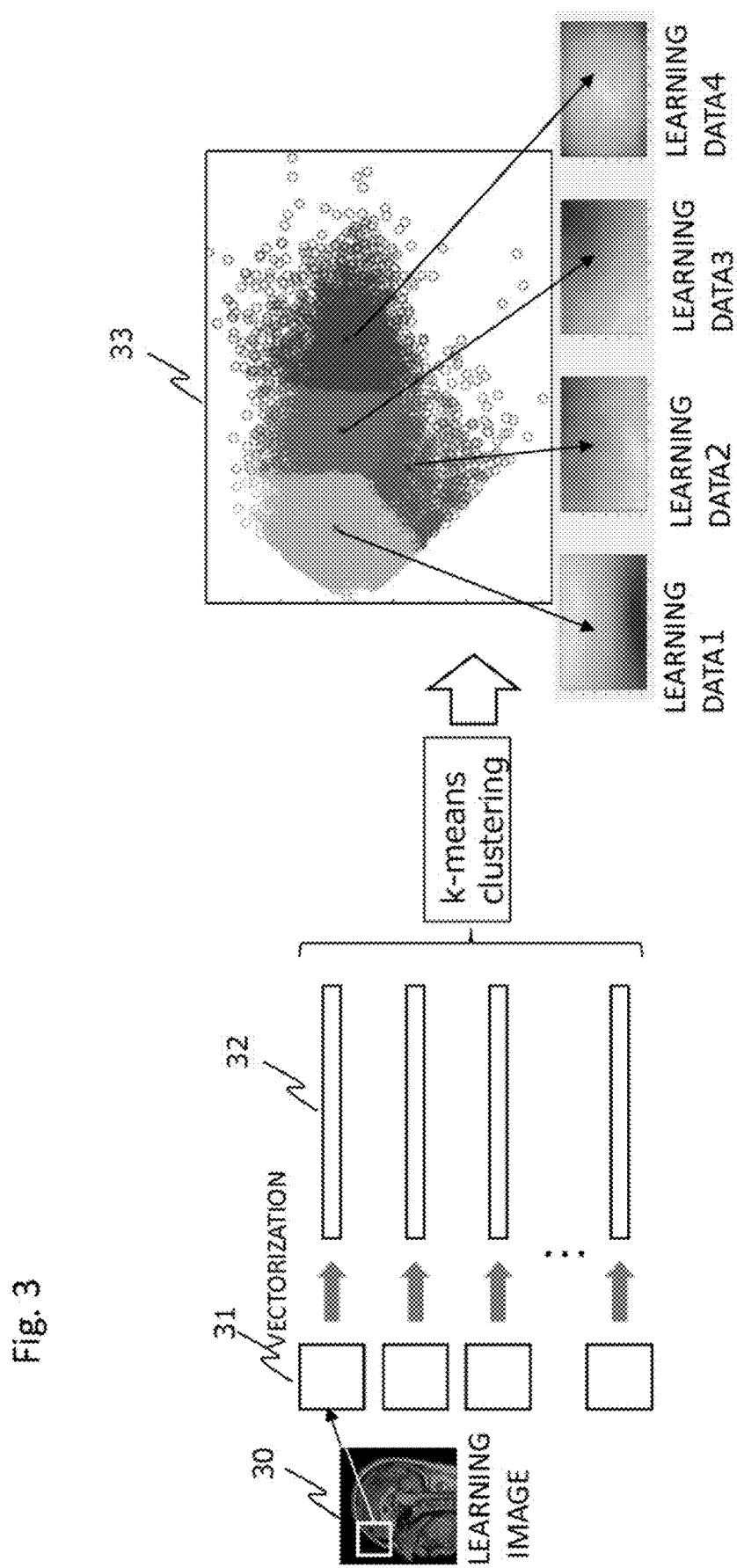
FIG. 3 is a diagram for explaining an example of processing of a classification unit.

First, a large number of patches cut out from a plurality of image data (hereinafter referred to as learning image) are clustered. An example of a method for clustering the patches cut out from the learning image is shown in FIG. 3. First, as shown in FIG. 3, the classification unit 220 cuts out patches 31 from a learning image 30 in advance and vectorizes them. For example, when a size of the patch is n×m pixels, a vector 32 including "n×m" vector elements is generated. The vectors are clustered, to determine each cluster so as not to overlap each other. Clustering is a method of classifying the image data (here, the patches) according to their features, and the features may include various feature amounts such as luminance, presence or absence of edge, and inclination of the edge.

As clustering, known clustering methods such as hierarchical clustering and non-hierarchical clustering (k-means method and its evolution, and EM algorithm and its evolution) can be used. However, the k-means method is preferred in that an amount of computation required for one iteration can be reduced.

A distribution diagram 33 is obtained by mapping the vector 32 of each patch to a space having a feature amount as the axis. Note that the distribution diagram 33 of FIG. 3 shows a simplified two-dimensional distribution diagram in which two feature amounts are a vertical axis and a horizontal axis. However, the number of feature amounts may be three or more. In an example shown in FIG. 3, a large number of patches constituting the learning image are classified into four clusters (learning data 1 to learning data 4)

by 4-means method. The learning data 1 having a feature that a step of luminance appears in a horizontal direction, the learning data 2 having a feature that the luminance changes continuously and the step is unclear, the learning data 3 having a feature that the step appears diagonally, and the learning data 4 having a feature that the luminance changes radially from a center are generated. The learning data are stored in the storage device 300 in advance.

Next, learning of the restorer using each learning data will be described.

The restorer 240 uses a pair of a correct image and an image with lower image quality (a degraded image) as the learning data, and has learned to output as an output image the image with minimum difference from the correct image for an input image, and the CNN is used in the present embodiment.

Figure 4:
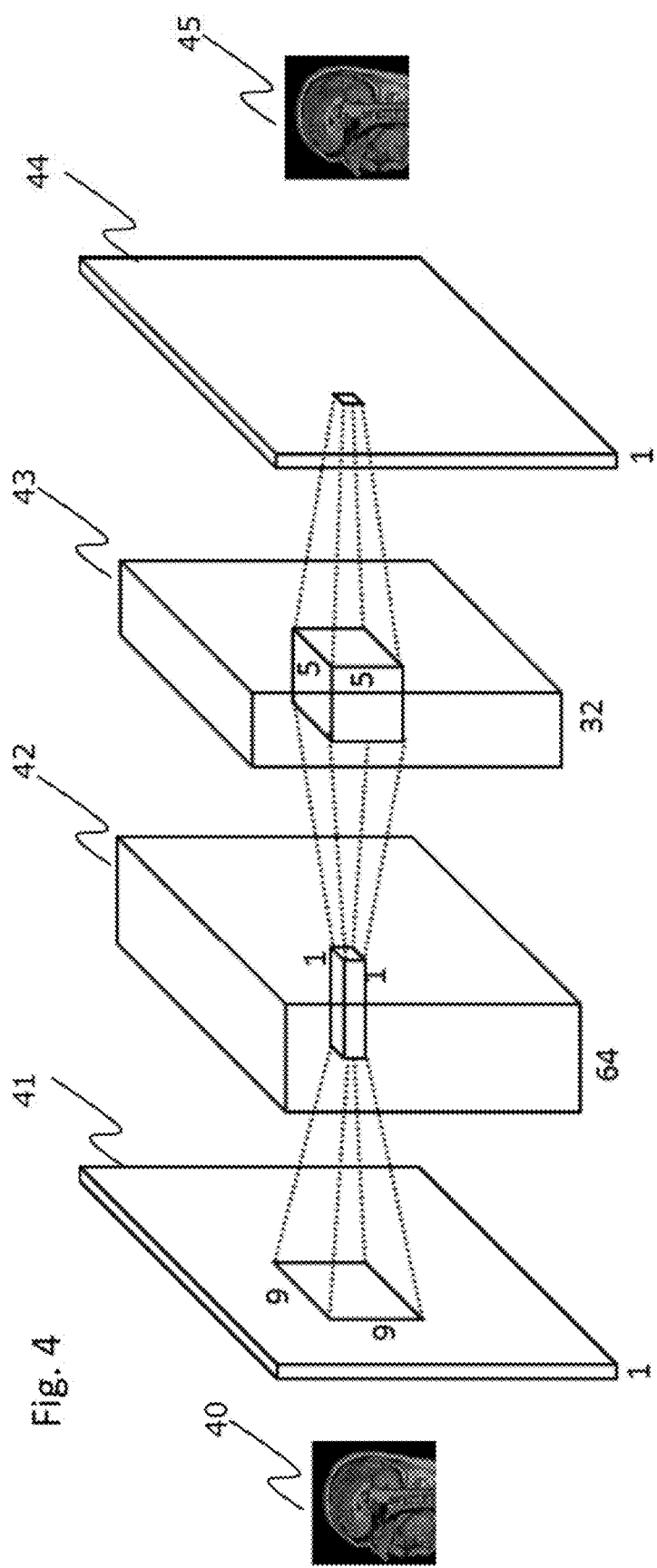
FIG. 4 is a view showing a structure of a restorer (CNN).

As schematically shown in FIG. 4, the CNN is a calculation unit constructed on a computer configured to repeat a large number of convolution operations 42 and pooling 43 on a multilayer network between an input layer 41 and an output layer 44. The CNN extracts the features of the input image by repeating the convolution operations and pooling for an input image 40 and outputs them as the output image 45. In the drawing, a number in front of a block indicating each layer is the number of layers, and the number in each layer indicates a size to be processed in the layer.

Figure 5:
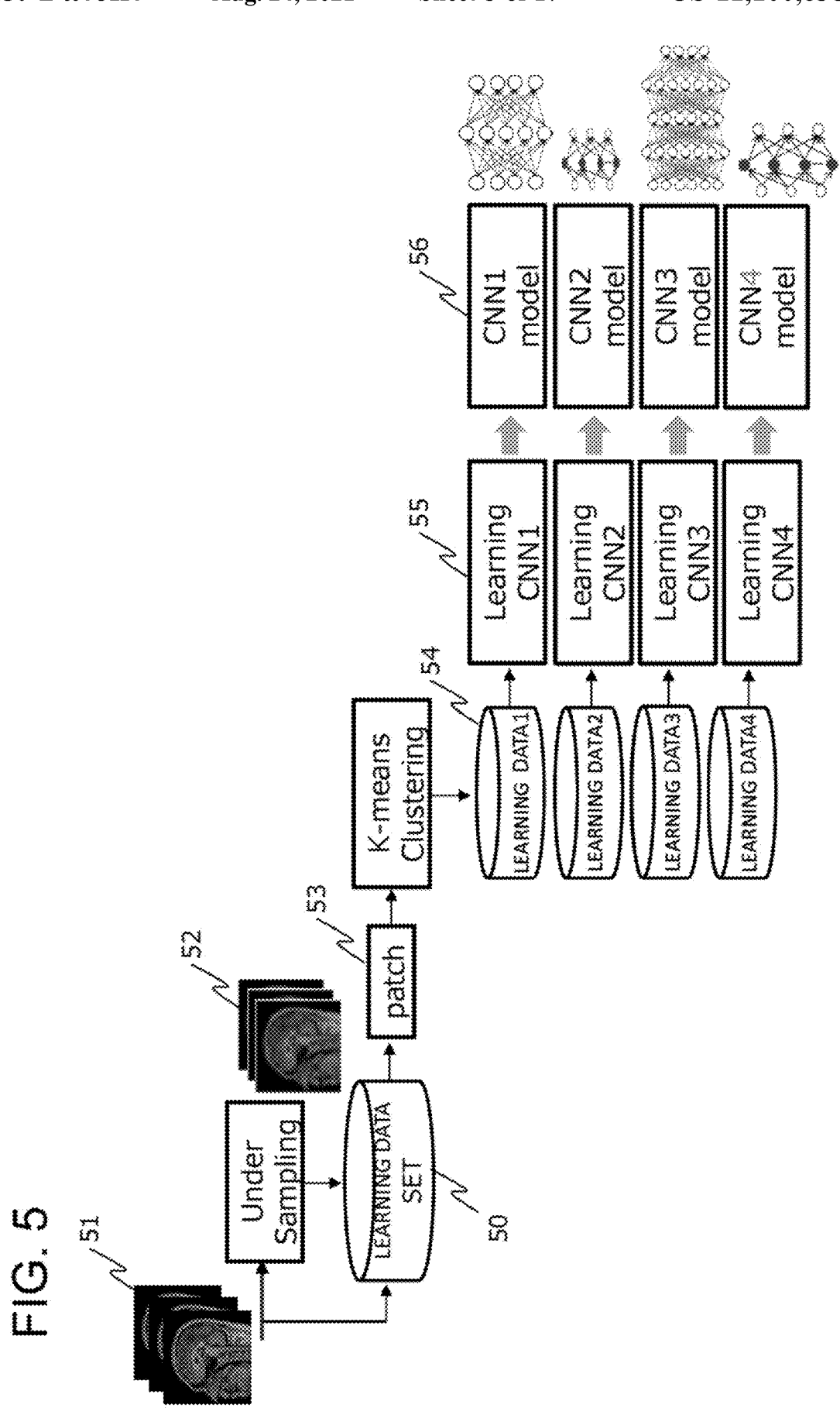
FIG. 5 is a diagram for explaining a learning process of the CNN.

Here, as a pair of learning images, as shown in FIG. 5, a learning dataset 50 including a pair of a correct image 51 and a test image 52 with a degraded image quality generated based on the correct image is used. This learning data is clustered for each patch 53, to be used as the input image for an unlearned CNN 55 for each cluster (each learning data) 54, and a process is repeated while changing parameters such as an activation function of each layer of the CNN and a weight between nodes, and a learning rate until a difference between the output image of the CNN and the correct image converges to a predetermined threshold value or less. The image quality of the test image is adjusted to be degraded depending on the imaging method (undersampling method) in the imaging unit 100. How to determine the image quality of the test image will be described in an embodiment for each modality described below.

The CNN in which the difference between the output image and the correct image finally converges to the predetermined threshold value or less is set as a learned CNN 56 corresponding to the cluster of the correct image. Thus, the same number of learned CNNs (CNN1 to CNN4 in FIG. 2) as the number of correct images (the number of types of the clusters) is obtained.

As the CNN, known software such as TensorFlow (Google LLC), Chainer (Preferred Networks Inc.), and Theano (Universite de Montreal) can be used.

Figure 6:
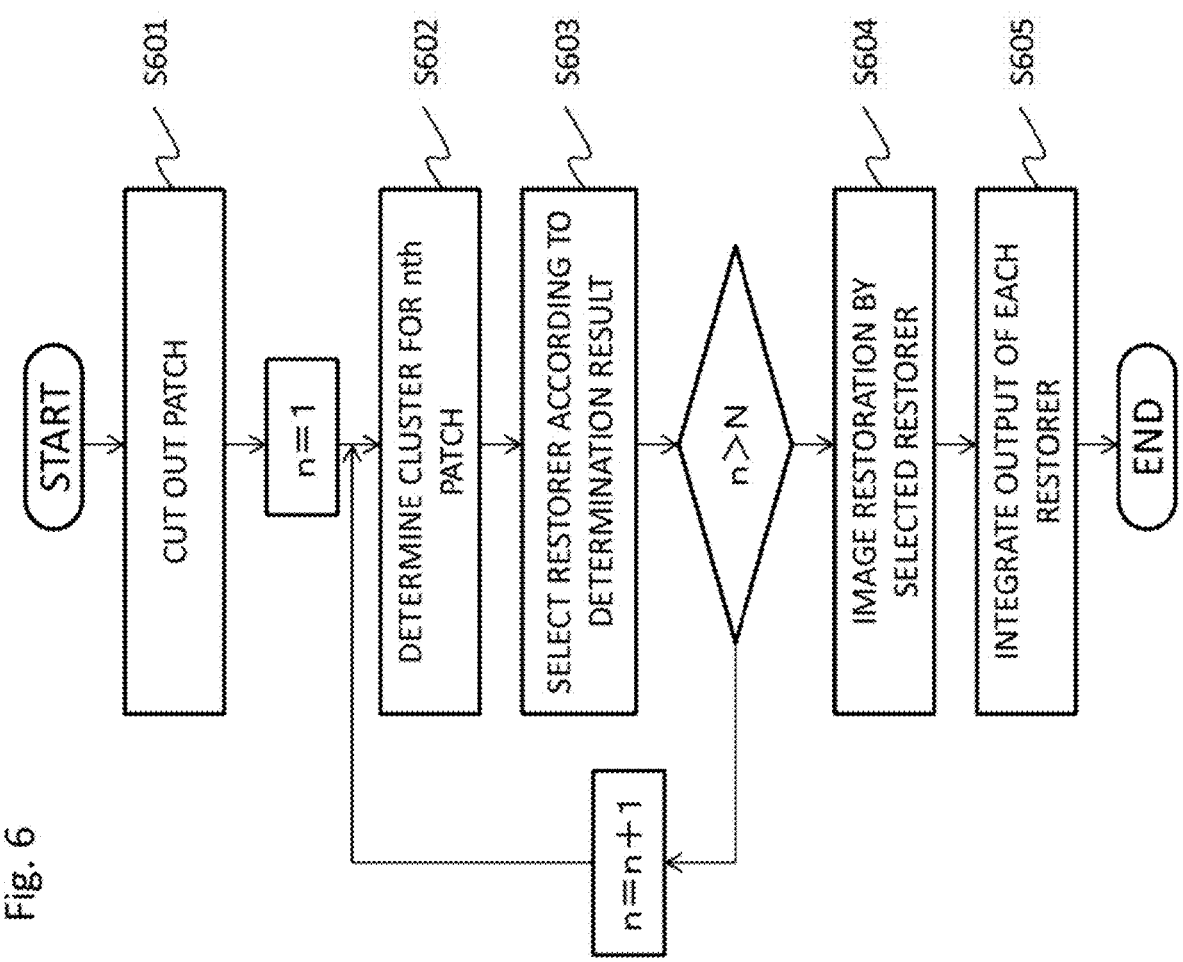
FIG. 6 is a diagram showing the operation flow of the image processing unit.

Next, an operation flow of the image processing unit 220 in which the learned CNN described above is incorporated as the restorer 240 will be described with reference to FIG. 6.

Figure 7:
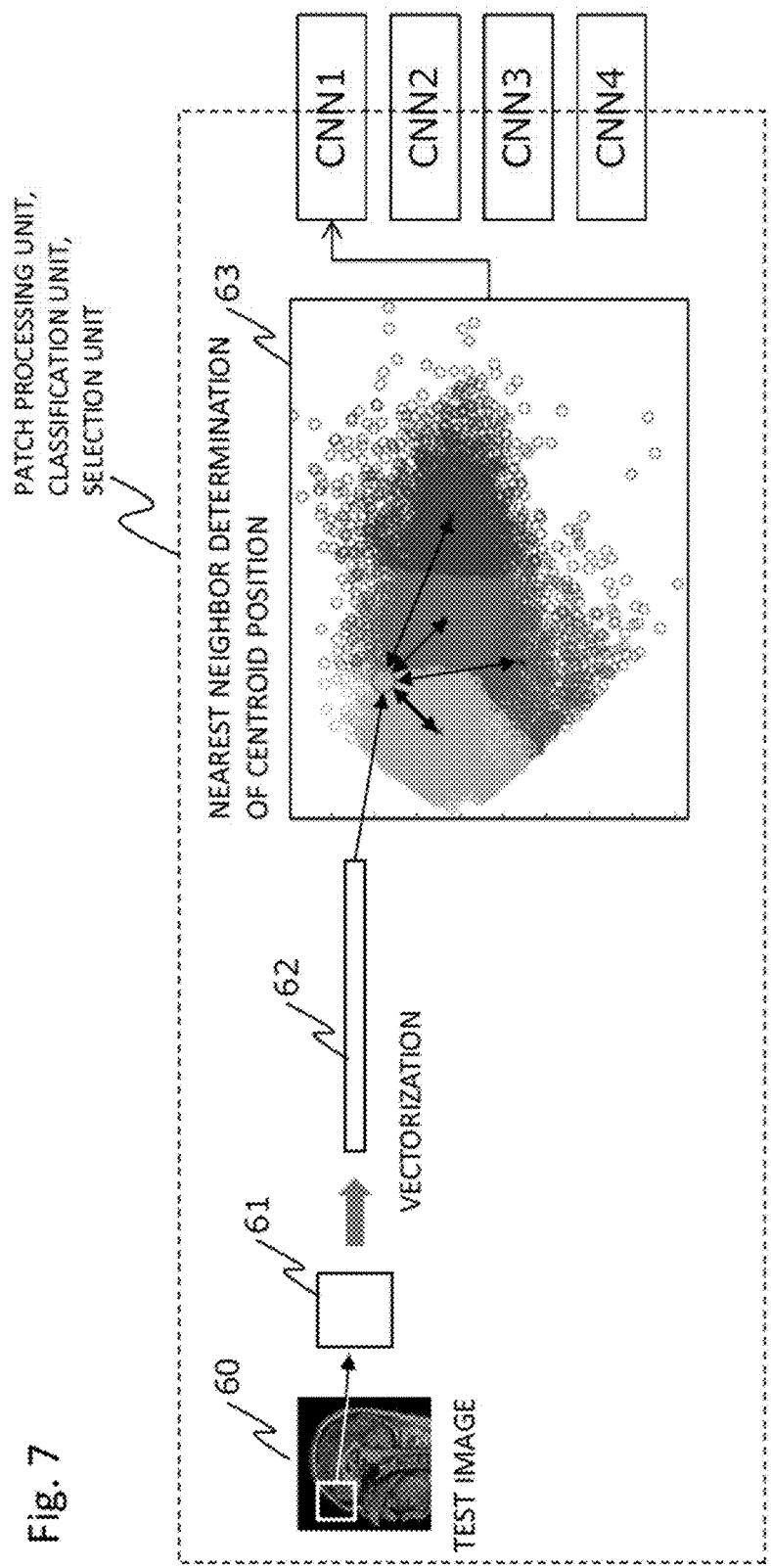
FIG. 7 is a diagram for explaining processing of a selection unit.

The image processing unit 200 receives the image data from the imaging unit 100, and first, cuts out the image data into the patches of a predetermined size in the patch processing unit 210, and passes them to the classification unit 220 (S601). The classification unit 220 classifies the patches into one of the plurality of clusters according to the features of the image (S602). A classification method is the same as the clustering method when the learning data (FIG. 3) is generated, and as shown in FIG. 7, a patch 61 is cut out from an image 60 to be processed, a vector 62 is generated, and a position on a distribution diagram 63 stored in advance in the storage device 300 is determined. The classification unit 220 determines which cluster the input patch belongs to by the nearest neighbor method using the distribution diagram. That is, the classification unit 220 calculates distances between centroids of the plurality of clusters included in the distribution diagram and a coordinate of the input patch in the distribution diagram, and determines the cluster having the smallest distance from the centroid as the cluster to which the patch 61 to be processed belongs.

Here, the patch 61 to be processed may have the same distance from two or more clusters. In such a case, one patch may be classified into two clusters, or may be treated as not being classified into any cluster. Further, the distance may be thresholded, and only when a distance from a certain cluster is less than or equal to a predetermined threshold value, the patch may be classified into the cluster, and when distances from all clusters are greater than or equal to the threshold value, the patch may be treated as not being classified into any cluster.

The selection unit 230 selects one of the plurality of restorers 240 according to results obtained by the classification unit 220 (S603). Each of the plurality of restorers 240 includes learned CNNs (CNN1 to CNN4 in FIG. 2) trained using the pair of learning images as described above.

Thus, the patch to be processed is input to the input layer of the selected CNN. For example, as shown in FIG. 7, the image data of the patch 61 classified as cluster 1 by the classification unit 220 is processed by the CNN 1 optimized for processing the image of the cluster 1 (S604). Thus, the output image with a high accuracy rate can be obtained. Note that the patch that is classified into two or more clusters in Step S602 may be processed by each CNN.

When the patch is cut out, clustering and CNN selection (S602 to S603) are performed for all patches of the image data to be processed, and then the process is performed in each CNN. Finally, the integration unit 250 integrates the output images of the restorers 240, and obtains the reconstructed image for all the patches, that is, the entire image data to be processed (S605). At this time, for example, when one patch is processed by two or more CNNs, an average value of the output images of the CNNs is calculated and used as the output image of the patch to perform integration.

As described above, according to the present embodiment, the image obtained by the imaging device or the image of the patch cut out from the image is classified into the plurality of clusters according to the features, and the plurality of restorers trained for each feature are prepared. Then, the restorer is selected and used according to the features of the image (patch) to be processed. By using the restorer that has been trained for each feature, it is possible to reproduce the image degraded due to undersampling during imaging in a short time, and to significantly reduce an overall imaging time from imaging to image reconstruction compared to compressed sensing. Further, since the patch is processed by selecting one or a few CNNs, processing load is reduced and processing time is reduced compared to ensemble learning in which the output is selected or synthesized after passing through all the CNNs.

Modification 1 of First Embodiment

Figure 8:
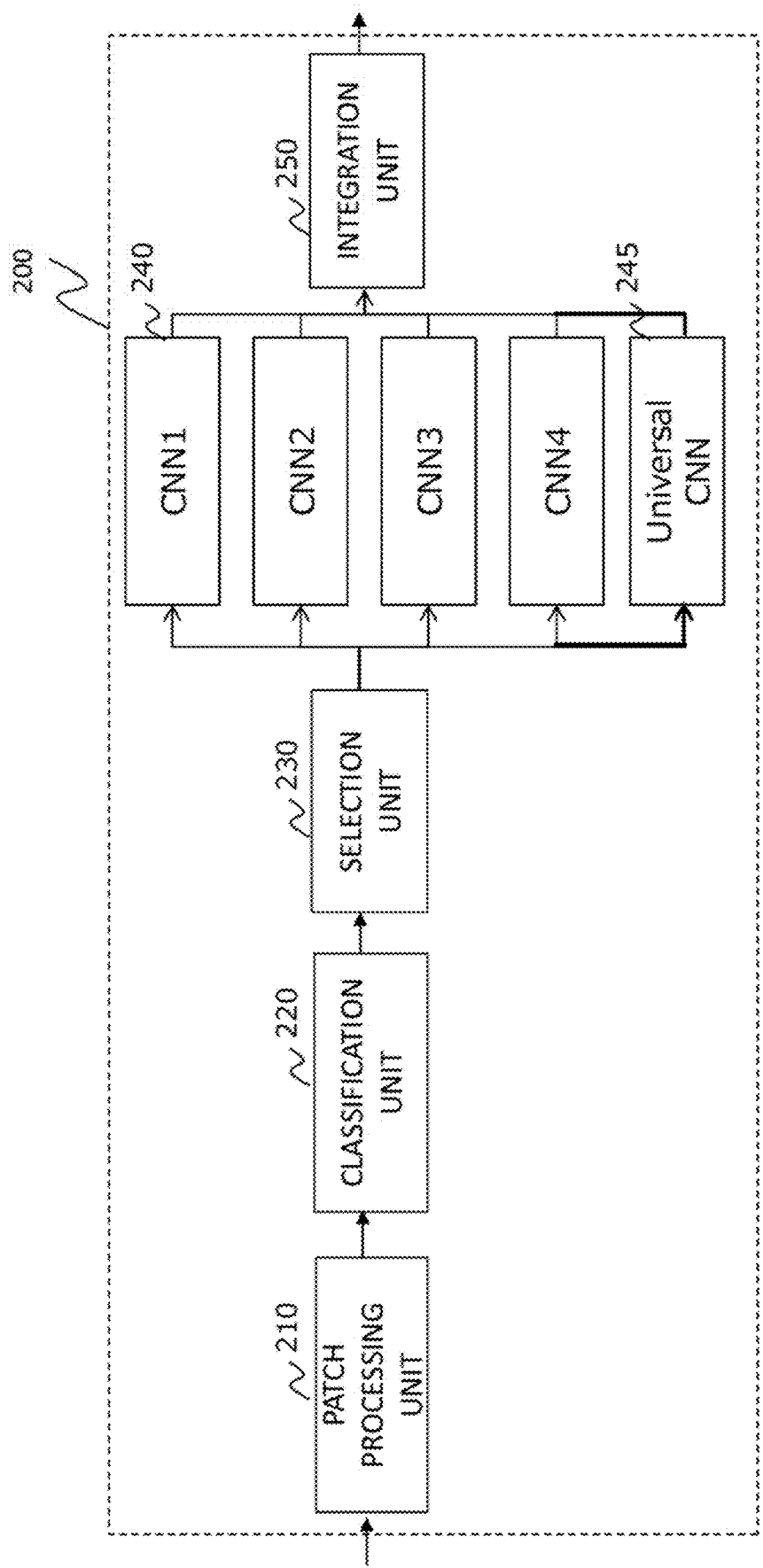
FIG. 8 is a diagram showing the configuration of the image processing unit of Modification 1 of the first embodiment.

In the first embodiment, the same number of restorers (CNNs) as the number of clusters are prepared. However, in this modification, a CNN (here, referred to as a universal CNN: UCNN) that is not associated with a specific feature is added. FIG. 8 shows a configuration example of the image processing unit 200. In the drawing, a "Universal CNN" 245 is the UCNN.

Examples of the UCNN include the CNN obtained by learning not the patch but the image itself (whole) as the learning image, and the CNN obtained by learning using a combination of patches at the center or periphery of each cluster as the learning image.

This modification is the same as the first embodiment in that the image data is classified into the clusters using the nearest neighbor method by the classification processing unit 220 after a patch process by the patch processing unit 210. However, the patch that cannot be clustered because the distances from two or more clusters are equal or the distance from any cluster exceeds the threshold value at the time of classification is passed to the UCNN 245 and processed. Thus, the image quality can be improved compared to a case where the patch that does not apply to a specific feature is processed by the CNN1 to the CNN4 learned about the feature.

Note that a method of using the UCNN is not limited to the case where it is applied to the above-mentioned patch that cannot be clustered. For example, the CNN corresponding to the cluster and the UCNN may be used in combination for the clustered patch. The image quality is expected to be improved by increasing the number of CNNs for processing.

Modification 2 of First Embodiment

Figure 9:
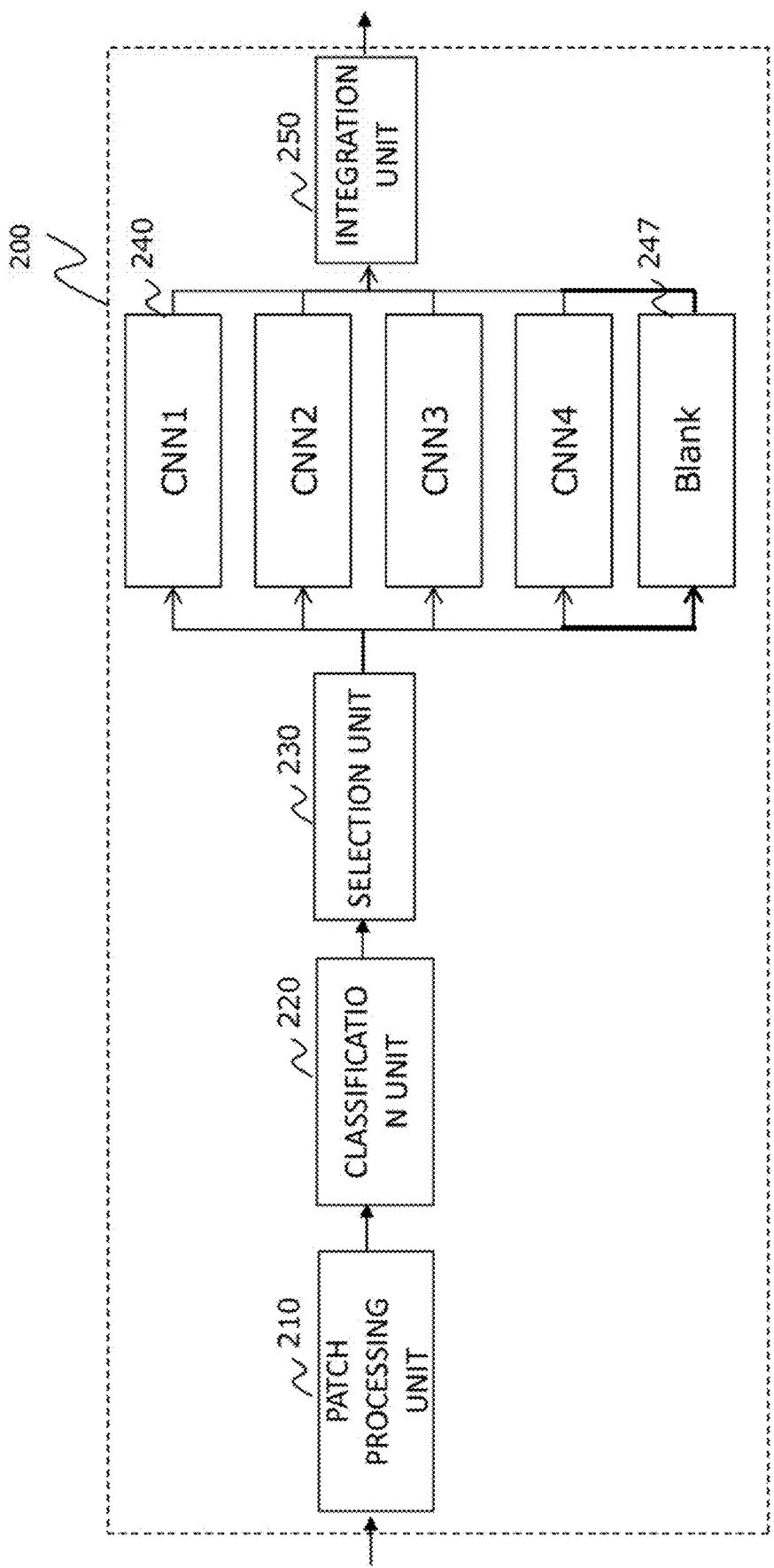
FIG. 9 is a diagram showing the configuration of the image processing unit of Modification 2 of the first embodiment.

In the first embodiment, all the patches cut out from the image data are processed by the prepared CNN. However, this embodiment is characterized by including a CNN blank 247. FIG. 9 shows a configuration example of the image processing unit 200. In this case, an input is an output as it is, that is, the patch cut out from the image data is input to the integration unit 250. The patch applied to the blank may be, for example, a patch that cannot be clustered, or may be the image data in a region outside a region of interest (ROI).

Figure 10:
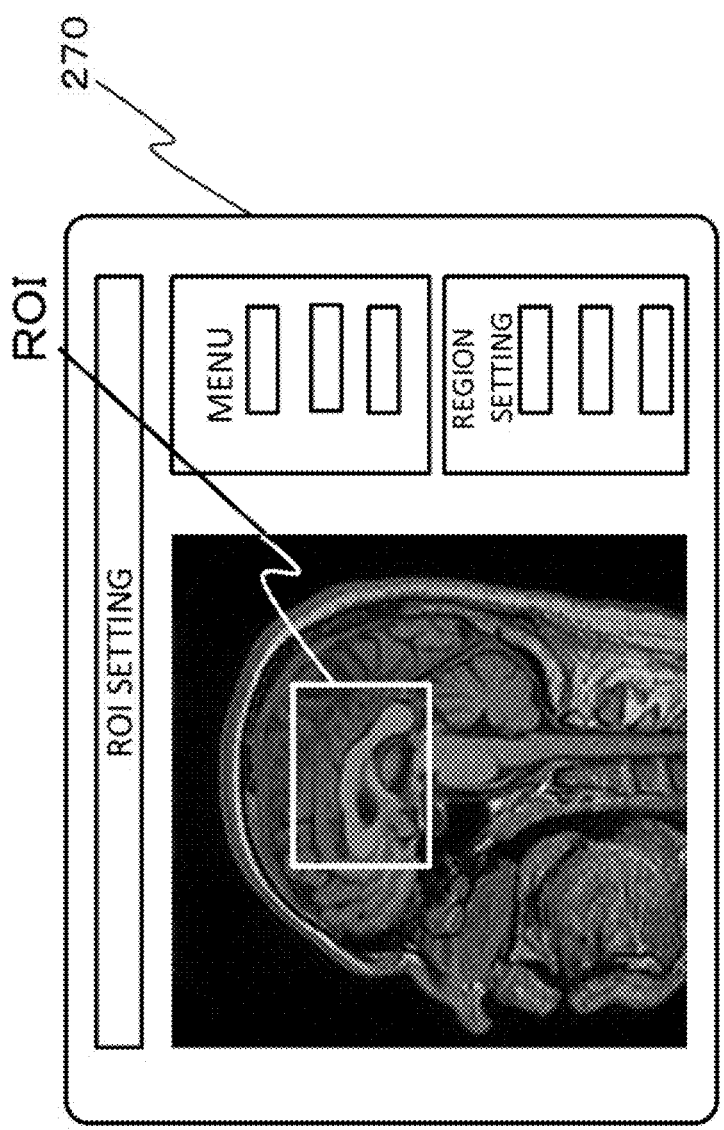
FIG. 10 is a view showing an example screen for setting an ROI.

In the latter case, a user may be allowed to set the ROI, for example, via a UI or the like (an ROI setting unit 270) as shown in FIG. 10. When the user sets the ROI, the image processing unit 200 uses the information to pass the image data of a portion not set to the ROI not to the classification unit 220 and the selection unit 230 but to the integration unit 250 through the blank. Thus, the image data in which only the ROI is converted to a high-quality image is obtained.

As described above, according to this modification, the entire processing time can be reduced by omitting CNN process for a portion having no feature or a portion outside the region of interest in the image.

Modification 3 of First Embodiment

In the first embodiment, the patch is cut out from the image data under a condition that the patches do not overlap each other. However, the patch processing unit 210 can also cut out adjacent patches in an overlapping manner. The image quality of the output image can be further improved by cutting out the patches in an overlapping manner and performing the CNN process. An overlapping ratio is not particularly limited, but, since a processing amount is increased and redundancy is also increased as the ratio is increased, it is preferably 50% or less from the viewpoint of reducing the processing time. Only a portion of the patches, for example, in the region of interest may be overlapped instead of overlapping all the patches.

Figure 11:
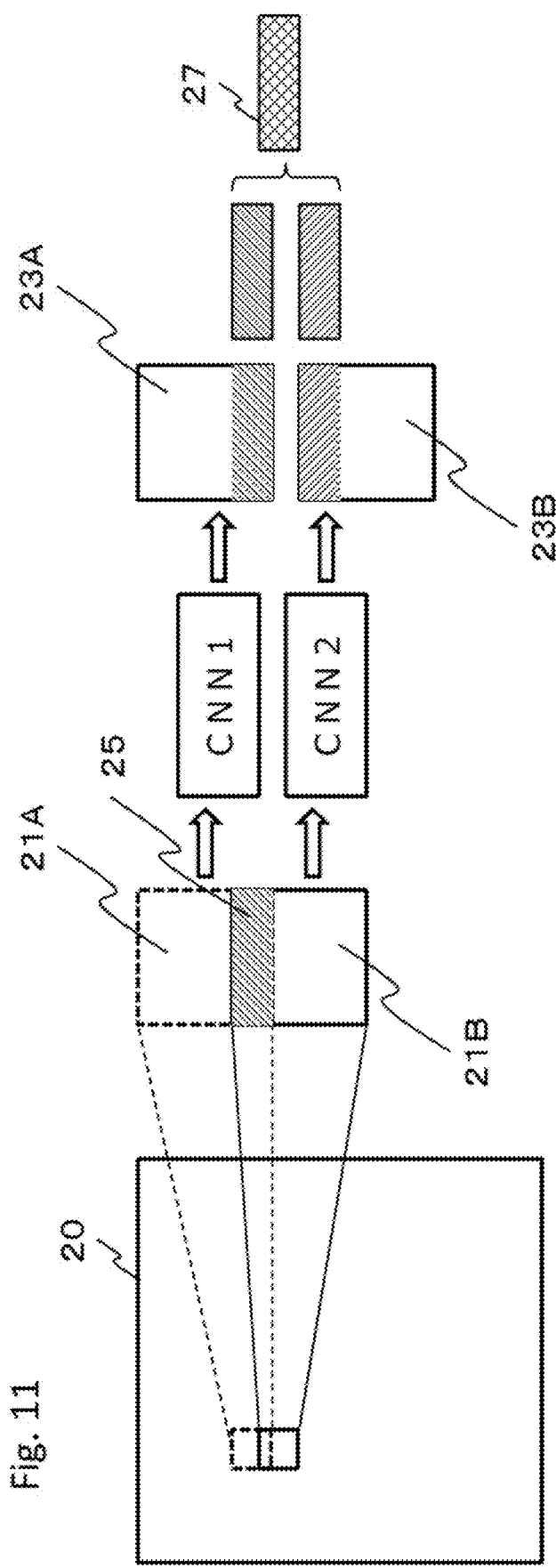
FIG. 11 is a diagram explaining a patch process of Modification 3 of the first embodiment.

When the patches are cut out in an overlapping manner, the clusters for the adjacent patches may be different in the classification unit 220 and the CNNs used may be different. In this case, as shown in FIG. 11, output images 23A and 23B are respectively obtained from different CNNs (CNN1 and CNN2 in FIG. 11) for an overlapping portion 25 between the patch 21A and the patch 21B. In this case, when the integration unit 250 synthesizes the outputs from the two CNNs, it performs processing such as taking an average value or adding weights as shown in the following formula (1) or (2) for the overlapping portion 25, to obtain data 27 of the overlapping portion. As the weights in the weighted addition, for example, distances (d1, d2) from a cluster center can be used. That is, the weight of the output data (overlap) from the CNN corresponding to a cluster is increased as the distance is shorter.

$$S(x,y) = \{S1(x,y) + S2(x,y)\}2 \tag{1}$$

$$S(x,y) = w1 \times S1(x,y) + w2 \times S2(x,y) \tag{2}$$

where, w1=d1 (d1+d2), w2=d2/(d1+d2)

S(x, y) is a pixel value after average or weighted average, and S1(x, y) and S2(x, y) are pixel values of output images from two CNNs.

According to this modification, by cutting out the patches in an overlapping manner, even when types of the CNNs used for the adjacent patches are different, it is possible to avoid discontinuity between the patches, thereby obtaining the output image with good image quality.

Hereinabove, the embodiment which can be used irrespective of a type of the imaging unit, and its modification has been described. Next, an embodiment for each modality will be described.

Second Embodiment

An embodiment in which the present invention is applied to the MRI device will be described.

Figure 12:
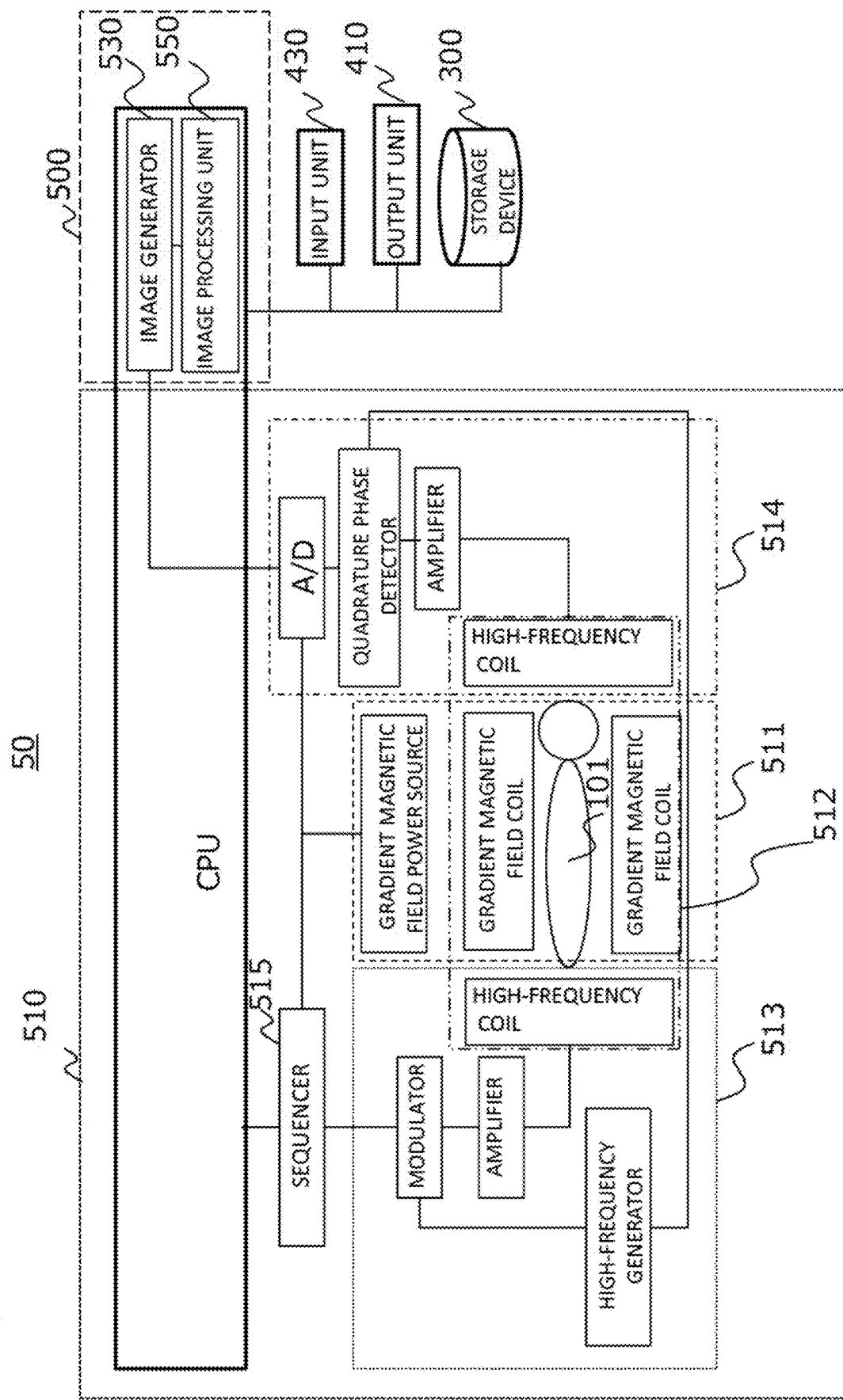
FIG. 12 is a diagram showing the overall configuration of the medical imaging device (MRI device) of a second embodiment.

As shown in FIG. 12, an MRI device 50 includes, as an MR imaging unit 510, a static magnetic field generator 511 including a static magnetic field generating magnet, a gradient magnetic field generator 512 including gradient magnetic field coils that generate gradient magnetic fields in three axial directions in a static magnetic field space generated by the static magnetic field generating magnet, a transmitting unit 513 including a high-frequency coil (transmitting coil) that applies a high-frequency magnetic field to the subject placed in the static magnetic field space, a receiving unit 514 including a high-frequency coil (receiving coil) that receives a nuclear magnetic resonance signal generated from a subject 101, and a sequencer 515 that controls an operation of the gradient magnetic field generator 512, the transmitting unit 513, and the receiving unit 514 according to a predetermined pulse sequence.

The gradient magnetic field generator 512 includes a gradient magnetic field power source for driving the gradient magnetic field coils in the three axial directions. The transmitter 513 includes a high-frequency generator, a high-frequency amplifier, a modulator, and the like for giving a predetermined high-frequency signal to the transmitting coil and irradiating an electromagnetic wave with a nuclear magnetic resonance frequency from the transmitting coil. The receiving unit 514 includes an amplifier that amplifies the signal detected by the receiving coil, a quadrature phase detector, and an A/D converter that converts the signal into a digital signal.

In addition to the imaging unit 510, the MRI device 50 includes a reconstruction unit 500 that performs a calculation such as image reconstruction using the nuclear magnetic resonance signal (digital signal) received by the receiving unit 514, an output unit 410 such as a display for displaying the generated image and the UI, and an input unit 430 such as an input device for inputting commands and information required for the imaging unit 510 and the reconstruction unit 500.

The reconstruction unit 500 includes: a storage device 300 that stores k-space data (nuclear magnetic resonance signals) obtained by the imaging unit 510, data in the middle of calculation, and numerical values such as parameters required for the calculation; an image generator 530 that performs a calculation such as inverse Fourier transform on the k-space data to convert the k-space data into real space data; and an image processing unit 550. A function of the reconstruction unit 500 is implemented by a memory and software installed in the CPU or the GPU. However, a part of the image generator 530 and the image processing unit 550 may be implemented by hardware.

The image processing unit 550 has the same function as the image processing unit 200 of the first embodiment. Referring to (B) of FIG. 1 showing the function of the image processing unit 200, the image processing unit 550 includes the image restoring unit including the classification unit 220, the selection unit 230, and the plurality of restorers 240. When the processing for each patch is performed, the patch processing unit 210 and the integration unit 250 are provided.

The restorer 240 constituting the image restoring unit includes a plurality of CNNs trained for each feature of the image data according to the imaging method (measurement data thinning method: undersampling) in an MR imaging unit 100. When there are a plurality of thinning methods employed by the imaging unit, a plurality of sets of restorers may be prepared according to the thinning method.

Hereinafter, the thinning method employed by the MR imaging unit 100 will be described.

In the MRI device 10, for example, in the case of 3D imaging, an encode gradient magnetic field is applied in a phase encoding direction and a slice direction to measure an echo signal, so that the k-space data is obtained. The k-space data is a data space having an axis in the encoding direction, and the number of encodings on each axis is determined by a size of FOV to be imaged. By repeating the pulse sequence while varying a magnitude of each encode gradient magnetic field, the k-space data having a predetermined number of encodings can be obtained. In the present embodiment, the data that has degraded by thinning or undersampling this encoding is obtained. Thus, the imaging time is reduced at a rate corresponding to a thinning rate.

Figure 13:
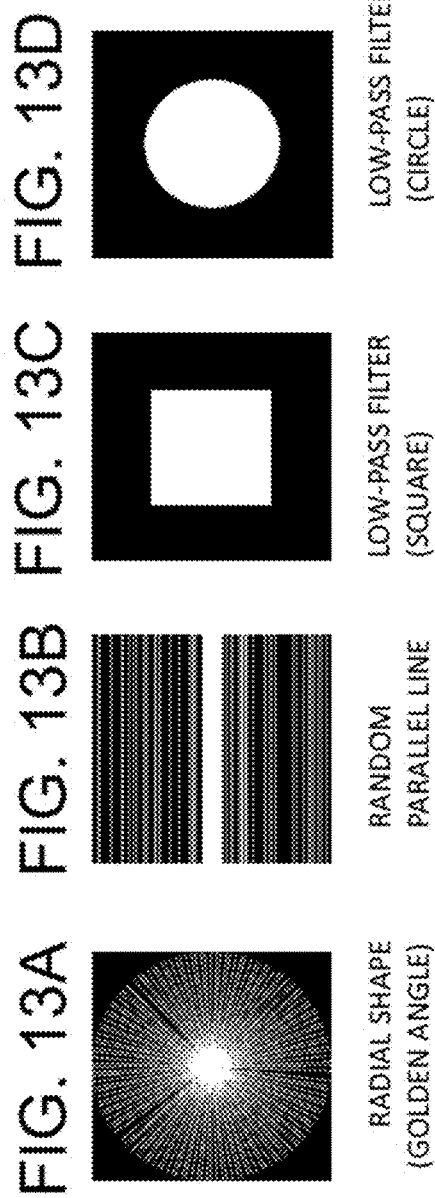
FIGS. 13A to 13D are views showing examples of undersampling in the second embodiment.

An example of undersampling is shown in FIG. 13. Here, in order to simplify explanation, a two-dimensional k-space is shown. In the drawing, a white portion is a sampled region, that is, a region where actual measurement data exists. (A) of FIG. 13 is a sample obtained by radially sampling the k-space, (B) is a sample obtained by sampling the k-space in a random parallel line shape, and (C) and (D) are samples obtained by sampling a central portion including an origin of the k-space in a rectangular or circular shape. The data of (C) and (D) can be generated using a low-pass filter.

Figure 14:
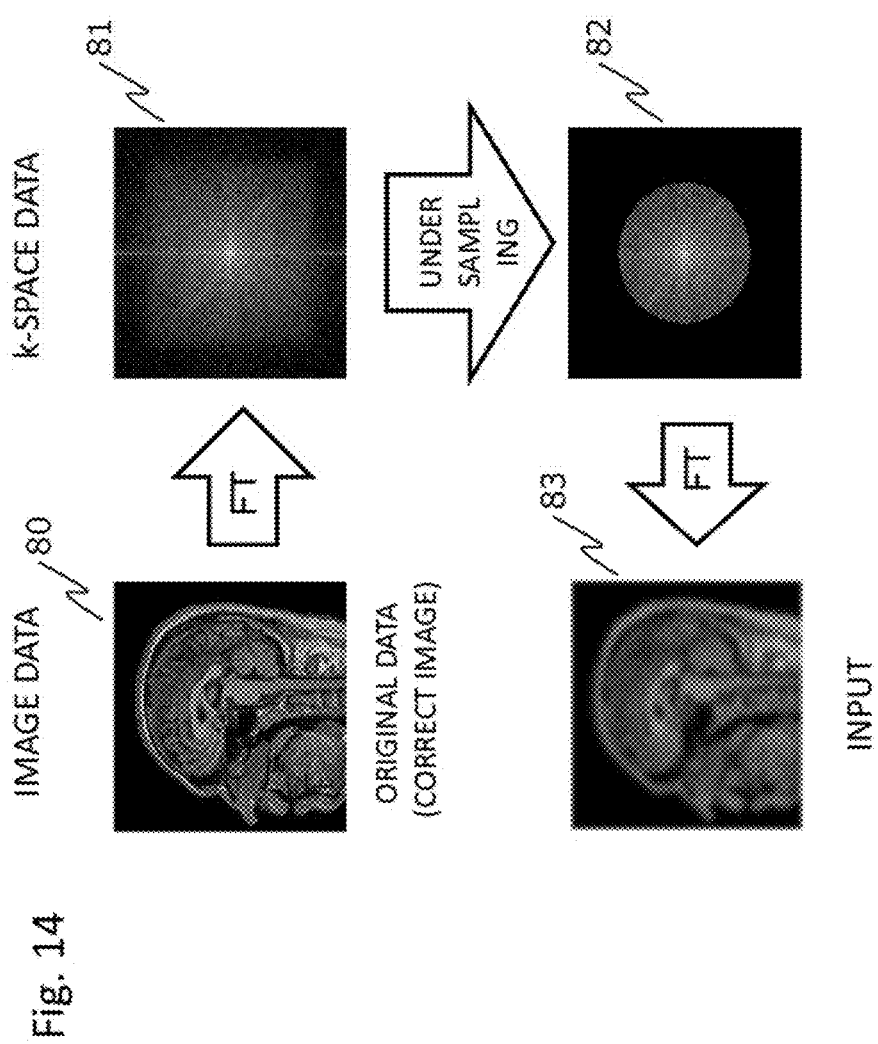
FIG. 14 is a diagram showing an example of a degradation process in the second embodiment.

The learning by the restorer 240 (CNN) is generation-type learning that brings the output image closer to the correct image in which the image reconstructed from the data obtained by measuring the predetermined number of encodings in the k-space is used as the correct image, and degradation data as shown in FIG. 13 is generated from the k-space data of the correct image. Then, the image reconstructed from the generated degradation data is used as the input image to the CNN, and the output image is brought closer to the correct image. This process is shown in FIG. 14. In this example, the correct image 80 is Fourier-transformed to generate k-space data 81. Next, a degradation process is performed on the k-space data 81 to obtain under-sampled k-space data 82. The degradation process is any one shown in (A) to (D) of FIG. 13. The k-space data 82 is inverse Fourier-transformed to reconstruct the image 83. Since the image 83 obtained in this way uses the k-space data 82 that has undergone the degradation process, the image 83 includes blur and the like. The image 83 is used as the input image to the CNN, and the process is repeated until an error between the output image from the CNN and the correct image becomes a predetermined value or less or the process reaches a predetermined number of repetitions. The parameters of the layers constituting the CNN, the number of nodes, and the like are changed for each repetition of the process.

Figure 15:
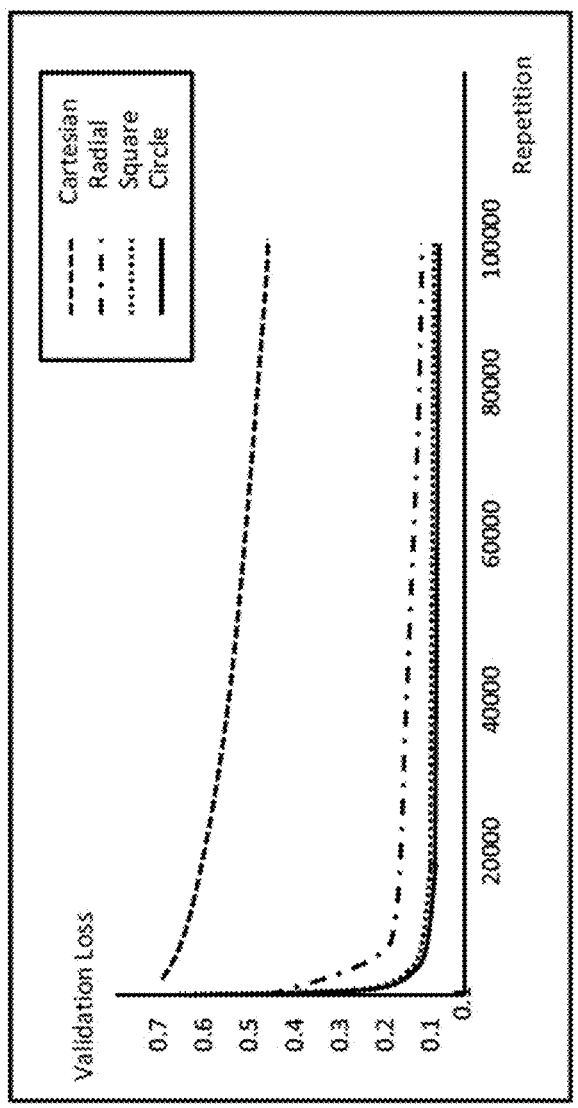
FIG. 15 is a diagram showing differences in convergence due to the degradation process in CNN training of the second embodiment.

FIG. 15 shows the degradation process of the above-described degraded image data 83 and a state of convergence of the process. As shown in the drawing, when the circular sampling shown in (D) of FIG. 13 is used, convergence occurs with the smallest number of repetitions. Therefore, as the degradation process in a learning stage of the CNN, the learned CNN can be formed most efficiently by the degradation using the low-pass filter. Further, experimentally, it has been confirmed that a final error is further reduced when a boundary between a circle and a region without data is blurred, or when a center of the circle is offset from the origin of the k-space, and it is effective as the degradation process for learning.

Prior to such generation-type learning, the patch processing unit and the classification unit of the image processing unit 550 cluster a large number of patches cut out from the correct image 80 and classify them into the plurality of clusters (learning data) for each feature (FIG. 5). The above-described generation-type learning by the CNN is performed for each cluster, and the CNN learned specifically for the cluster is obtained. That is, the plurality of CNNs corresponding to the plurality of clusters are obtained. Note that CNN learning may be performed on the MRI device by incorporating the CNN before learning into the reconstruction unit 500 (image processing unit 550) of the MRI device, or may be performed on an image processing device (computer) different from the MRI device, and the learned CNN may be implemented on the image processing unit 550 of the MRI device.

Thus, after the image processing unit 550 performs clustering and generates the learned CNNs, imaging and image processing are started. At the time of imaging, the k-space data is collected by an arbitrary imaging method, and the image generator 530 generates the image data in a real space. Although the imaging method is arbitrary, in order to reduce the imaging time, for example, undersampling at a double speed or higher is performed to obtain the image that has undergone the degradation process. The degradation process is not necessarily the same as learning of CNN. If the image is folded by undersampling, the image generator 530 performs a folding removal operation such as a SENSE method using sensitivity distribution of the receiving coil, and generates the image without a folding.

The image processing unit 550 performs clustering and image reconstruction using the learned CNN corresponding to the cluster on the image data generated by the image generator 530 as described in the first embodiment or its modifications (Step S601 to S605 in FIG. 6), and obtains a final image. This process has a shorter processing time than an image restoration process using a conventional CS technique, and the image with good image quality can be obtained without impairing an imaging shortening effect by undersampling.

According to the medical imaging device (MRI device) of the present embodiment, a low-quality image obtained in a short time by undersampling can be made to have the same quality as the image obtained by normal sampling without extending time required for image processing. In particular, by using the learned CNN adapted to features of the cluster for the image data after clustering, it is possible to reduce the image processing time while maintaining the image quality of the final image as compared to ensemble learning using the plurality of CNNs.

Further, according to the MRI device of the present embodiment, the learned CNN that can output the image with higher image quality in a short repetition time can be formed by selecting a specific degradation process in a learning process of the CNN.

Third Embodiment

An embodiment in which the present invention is applied to the ultrasonic imaging device will be described.

Figure 16:
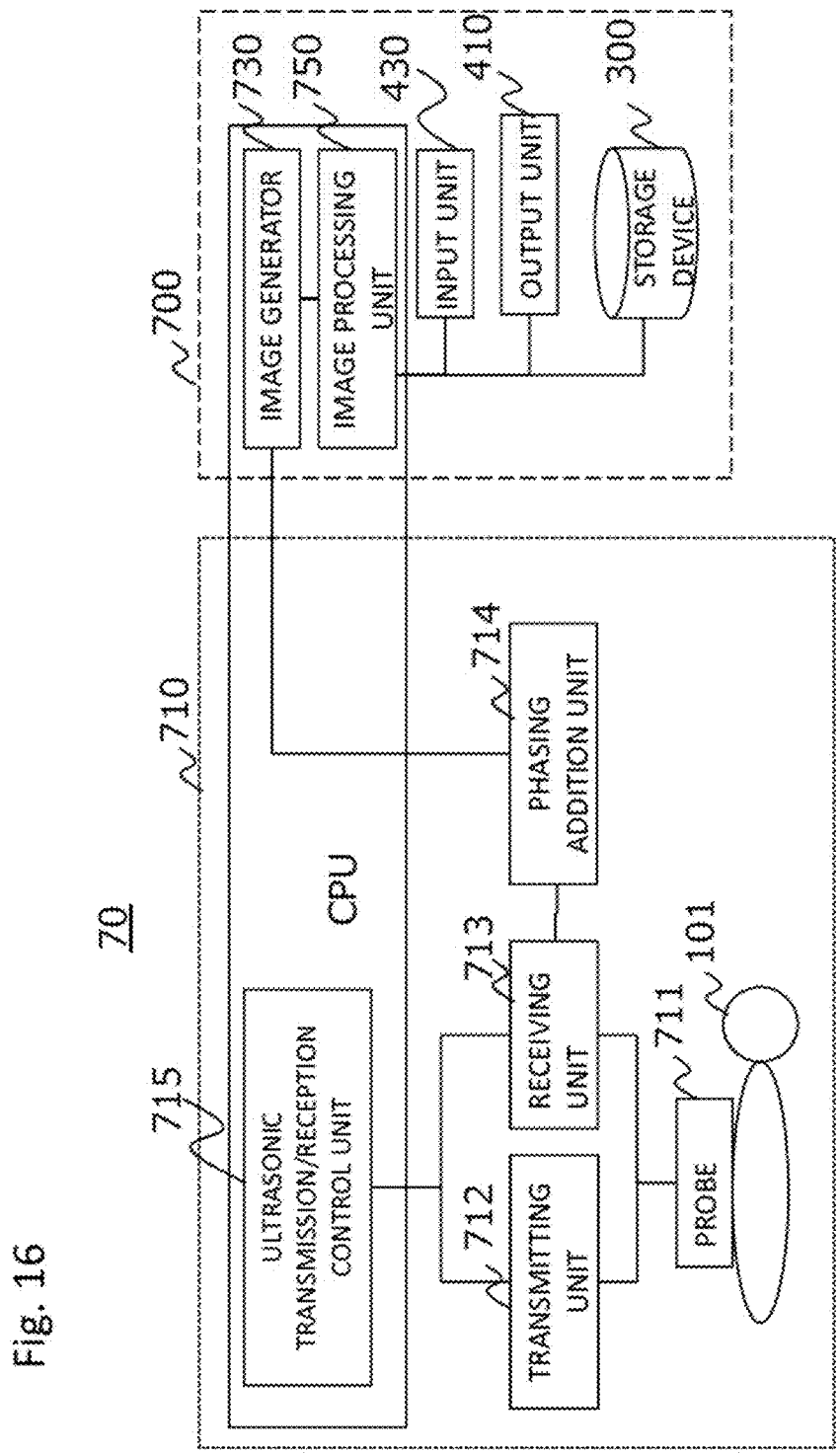
FIG. 16 is a diagram showing the overall configuration of the medical imaging device (an ultrasonic imaging device) of a third embodiment.

FIG. 16 shows an overall outline of an ultrasonic imaging device 70. This device is roughly divided into an ultrasonic imaging unit 710 and a reconstruction unit 700. The ultrasonic imaging unit 710 corresponds to the imaging unit 100 of the first embodiment and has the same configuration as a conventional ultrasonic imaging device. That is, the ultrasonic imaging unit 710 includes an ultrasonic probe 711 that transmits an ultrasonic wave, a transmitting unit 712 that transmits an ultrasonic drive signal to the probe 711, an ultrasonic receiving unit 713 that receives an ultrasonic signal (RF signal) from the probe 711, a phasing addition unit 715 that performs phasing addition (beam forming) on the signal received by the ultrasonic receiving unit 713, and an ultrasonic transmission/reception control unit 714 that controls the ultrasonic transmitting unit 712 and the ultrasonic receiving unit 713.

The reconstruction unit 700 includes an ultrasonic image generator 730 that generates an ultrasonic image such as a B-mode image and an M-mode image, and an image processing unit 750 having a function corresponding to the image processing unit 200 of the first embodiment. The reconstruction unit 700 may further include a Doppler processing unit (not shown) or the like. In an illustrated configuration example, the ultrasonic transmission/reception control unit 714 and the reconstruction unit 700 are built in one CPU, and the reconstruction unit 700 includes the input unit 430 for inputting processing conditions, data necessary for processing, and the like, the output unit 410 for outputting the image generated by the image processing unit 750 or the like, and the storage device 300 for storing data being processed, result images and the like. The ultrasonic transmission/reception control unit 714 may be built in a CPU different from the reconstruction unit 700, and may be a combination of hardware such as a transmission/reception circuit and control software.

The function of the image processing unit 750 is the same as the image processing unit 200 of the first embodiment. As shown in (B) of FIG. 1, the image processing unit 750 includes, for example, the patch processing unit 210, the classification unit 220, the selection unit 230, the plurality of restorers 240, and the integration unit 250.

There are various types of the ultrasonic probe 711. Generally, the ultrasonic probe 711 includes a large number of transducers arranged in a one-dimensional direction or a two-dimensional direction, and repeats transmission and reception of the ultrasonic wave while electronically switching the transducers at high speed. Resolution and artifacts in ultrasonic imaging are affected by probe frequency, device transmission/reception conditions, transducer element pitch, and the like. In general, depth can be deeper as the frequency is lower, but, the resolution is reduced. Further, the artifacts can be reduced by reducing the element pitch and increasing the number of transducers, or by reducing the frequency. However, an increase in the number of transducers leads to an increase in circuit scale of the device, which is limited. Furthermore, there are also restrictions on the transmission/reception conditions for the device.

The image processing unit 750 improves the image quality by applying the restorer 240 to the ultrasonic image captured under such restrictions. For example, the ultrasonic image captured under conditions that generate the highest image quality without restrictions such as the imaging time, or the ultrasonic image captured using a high-specification model, and the ultrasonic image that has undergone a predetermined degradation process are used as the learning data, and are clustered, to prepare the restorer 240 trained for each cluster.

In the imaging, the ultrasonic imaging unit 710 performs phasing addition on the ultrasonic wave received by the probe 711, and the ultrasonic image generator 730 generates the ultrasonic image. Similar to the first embodiment, the image processing unit 750 first receives the ultrasonic image created by the ultrasound image generator 730, performs patch processing and clustering, and then selects the restorer (CNN) applied to each cluster. Each CNN receives the data of the patch and outputs the data with improved image quality. Finally, the data from each CNN is integrated into the ultrasonic image.

The modifications of the first embodiment may also be applied to the present embodiment and the universal CNN may be added or the blank may be provided as the restorer. Only a desired region out of the ultrasonic image may be processed by the image processing unit 750 described above, or the patches may be cut out in an overlapping manner. Further, when the outputs of the CNNs are integrated, the weight may be given based on the distance from the cluster centroid of the patch to be processed.

Further, in the present embodiment, the case of improving the image quality degraded due to imaging conditions such as frequency and device restrictions such as the element pitch has been described. The present embodiment can also be applied to the data that has been undersampled by controlling a driving method of a number of elements, for example, by thinning the elements at random, the data that has been captured at a low frequency at the expense of resolution in order to increase the depth, or the like.

According to the present embodiment, in the ultrasonic imaging device, it is possible to compensate for reduction in resolution of the image quality due to restrictions on the device and the like, thereby obtaining the ultrasonic image with high image quality. In general, the ultrasonic device displays the image in real time simultaneously with imaging. According to the present embodiment, the image processing using the learned CNN is performed, so that a real-time property of image display is not impaired.

Fourth Embodiment

An embodiment when the imaging unit 100 is the CT device will be described.

Figure 17:
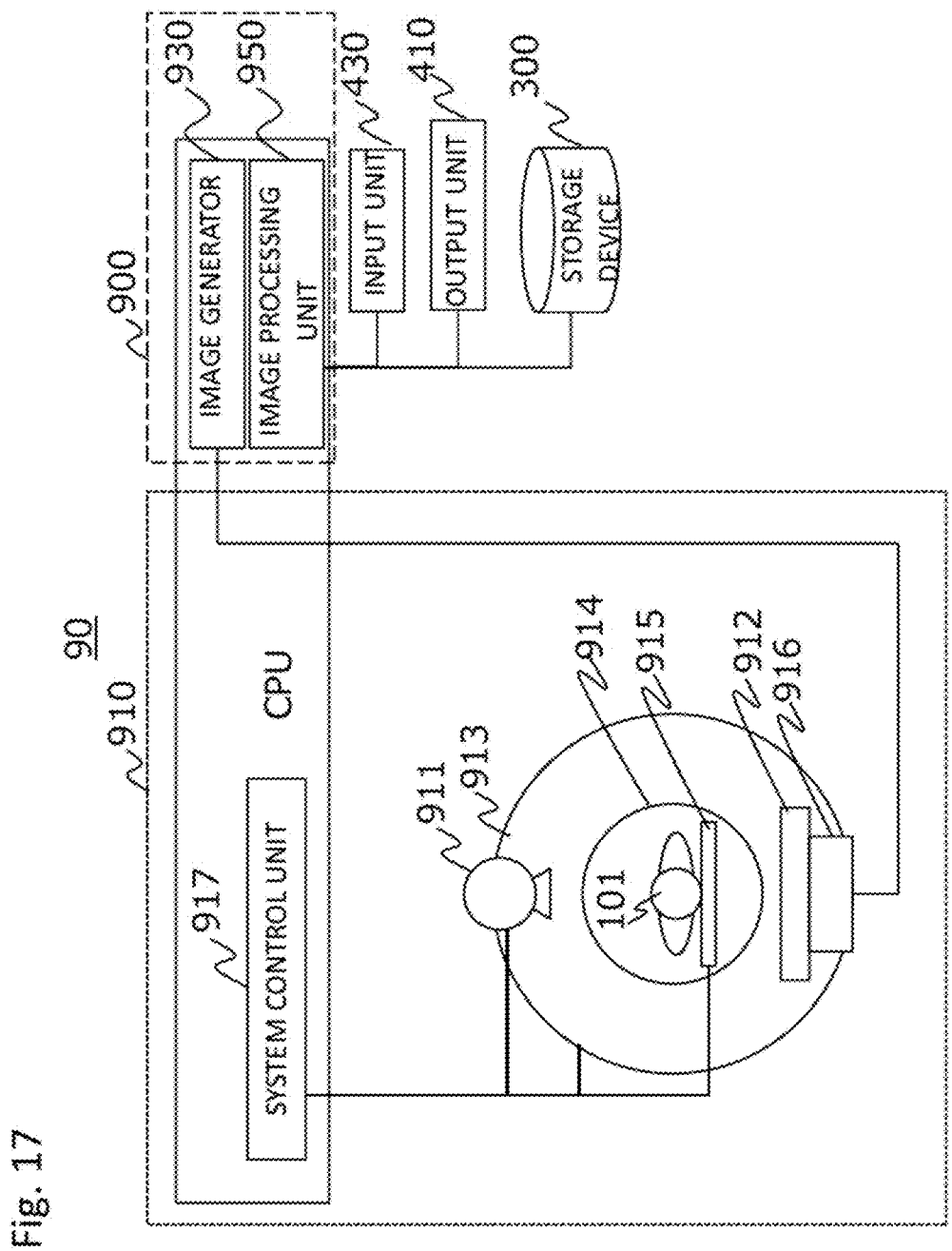
FIG. 17 is a diagram showing the overall configuration of the medical imaging device (a CT device) of a fourth embodiment.

An overall outline of a CT device 90 is shown in FIG. 17. This device roughly includes a CT imaging unit 910 and a reconstruction unit 900. The CT imaging unit 910 corresponds to the imaging unit 100 of the first embodiment and has the same configuration as a conventional CT device. That is, the CT imaging unit 910 includes an X-ray source 911 with an X-ray tube, an X-ray detector 912 in which a large number of X-ray detection elements including a solid-state detector, a diode and the like are arranged in a one-dimensional direction or an arc shape and a direction perpendicular thereto, a rotating plate 913 provided with an opening 914 at a center thereof and supporting the X-ray source 911 and the X-ray detector 912 at positions facing each other, a bed 915 on which the subject 101 is mounted in a space in the opening 914, a data collection unit 916 that collects an output of the X-ray detector 912 for each projection data, and a system control unit 917 that controls an operation of each element constituting the CT imaging unit 910.

The reconstruction unit 900 includes a tomographic image generator 930 that generates a tomographic image by performing operations such as back projection or successive approximation using the projection data collected by the data collection unit 916, and an image processing unit 950 having a function corresponding to the image processing unit 200 of the first embodiment. In an illustrated configuration example, the system control unit 917 and the reconstruction unit 900 are built in one CPU. The reconstruction unit 900 includes the input unit 430 for inputting the processing conditions, the data necessary for the processing, and the like, the output unit 410 for outputting the image generated by the reconstruction unit 900 or the like, and the storage device 300 for storing the data being processed, the result images and the like. The system control unit 917 may be built in the CPU different from the reconstruction unit 900, and may be a combination of hardware and control software. Similarly, a part of the reconstruction unit 900, for example, a part of function of the tomographic image generator 930 can be configured with hardware.

In the CT device 90, the X-ray irradiated radially from the X-ray source 911 and transmitted through the subject are detected by the X-ray detector 912 disposed facing the X-ray source. The projection data for each rotation angle is obtained by performing X-ray irradiation and detection at each rotation angle while rotating the rotating plate 913 at high speed. In general, the projection data is represented by a sinogram arranged in a data space in which the horizontal axis is an arrangement direction of the X-ray detection elements and the vertical axis is the rotation angle. In the case of helical scanning, the bed 915 is moved along with rotation of the rotating plate 913, to obtain three-dimensional projection data.

Here, the resolution of CT imaging is determined by a pitch of the detection elements constituting the X-ray detector 912, a rotational speed of the rotating plate 913, and a moving speed of the bed 915 relative to the rotational speed of the rotating plate 913 in the case of helical scanning, and the like. For example, when the rotational speed of the rotating plate 913 is fast relative to the exposure timing, an interval between rotation angles in the sinogram increases, and the resolution in a rotation angle direction is deteriorated. Further, when the X-ray detection elements are thinned and driven, the resolution in the arrangement direction of the detection elements is also degraded. Furthermore, when the X-ray irradiation angle (spread) is θ (degrees), the rotation angle of the rotating plate 913 needs to be "180°+↓" or more in order to reconstruct one tomographic image. For example, the data with a rotation angle of 180° is also the data with degraded image quality.

The image processing unit 950 of the present embodiment sets, as a process target, the image obtained under a condition that can reduce the imaging time as described above but provides a resolution lower than the original obtainable resolution, and performs reconstruction of the image having the original resolution. Specifically, the tomographic image generated by the tomographic image generator 930 using the data that has been undersampled in this way is input, and the data having the same image quality as the image that is not undersampled is generated. For this purpose, the restorer 240 trained as follows is prepared in the image processing unit 950. The restorer 240 is trained using as a pair of learning data the tomographic image (correct image) reconstructed without undersampling and the tomographic image (image that has undergone the degradation process) reconstructed by performing predetermined undersampling. In a learning phase of the restorer, the patches cutout from the correct image are clustered, the restorer is trained for each cluster, and the CNN for each cluster is created.

In consideration of differences in methods of undersampling (degradation process) during imaging, it is preferred to prepare plural sets of restorers trained with different learning data. In that case, according to an undersampling method employed at the time of imaging, a set of restorers trained for the undersampling is selected from the plural sets of restorers and used.

In the imaging, the tomographic image generator 930 generates the tomographic image using the projection data collected by the data collection unit 916 in the CT imaging unit 910. Similar to the first embodiment, the image processing unit 950 performs patch processing and clustering on the input tomographic image, and then selects the restorer (CNN) to be used for each cluster. Each CNN receives the image data of the patch and outputs the image data with improved image quality. Finally, the data from each CNN is integrated into the tomographic image. The modifications described in the first embodiment can also be applied to the present embodiment as appropriate.

According to the present embodiment, similarly to the second embodiment and the third embodiment, by processing the image obtained by reducing the imaging time and undersampling, or the image with low image quality due to the restrictions on the device, or the like, it is possible to reconstruct in a short time the image with the same image quality as the image obtained under conditions without undersampling or under conditions where the device is free from the restrictions.

DESCRIPTION OF REFERENCE NUMERALS AND SIGNS

10: medical imaging device, 50: MM device, 70: ultrasonic imaging device, 90: CT device, 100: imaging unit, 200: image processing unit, 210: patch processing unit, 220: classification unit, 230: restorer selection unit (selection unit), 240: image restoring unit (restorer), 250: integration unit, 270: ROI setting unit, 300: storage device, 410: output unit, 430: input unit, 500: reconstruction unit, 510: MR imaging unit, 511: static magnetic field generator, 512: gradient magnetic field generator, 513: RF transmitting unit, 514: RF receiving unit, 515: sequence control unit, 530: image generator, 550: image processing unit, 700: reconstruction unit, 710: ultrasonic imaging unit, 711: ultrasonic probe, 712: ultrasonic transmitting unit, 713: ultrasonic receiving unit, 715: phasing addition unit, 714: ultrasonic transmission/reception control unit, 730: ultrasonic image generator, 750: image processing unit, 900: reconstruction unit, 910: CT imaging unit, 911: X-ray source, 912: X-ray detector, 913: rotating plate, 916: data collection unit, 930: tomographic image generator, 950: image processing unit.

The invention claimed is:

1. A medical imaging device comprising:
   an imaging unit that collects image data from an inspection object; and
   an image processing unit that reconstructs an image using the image data collected by the imaging unit, wherein the image processing unit comprises:
   a classification unit that classifies the image data;
   an image restoring unit including a plurality of restorers corresponding to classifications by the classification unit; and
   a restorer selection unit that selects one or more restorers from the plurality of restorers according to classification results by the classification unit, and
   each of the plurality of restorers is a restorer including a neural network trained using learning data including a combination of a correct image and a degraded image for each classification, and for restoring the image with high image quality from an input degraded image.

2. The medical imaging device according to claim 1, wherein the image processing unit further comprises:
   a patch processing unit that cuts out image data patches from the image data collected by the imaging unit and passes them to the classification unit; and
   an integration unit that integrates output data processed for each image data patch in the image restoring unit.

3. The medical imaging device according to claim 2, wherein
   the patch processing unit cuts out the image data patches so that adjacent patches overlap each other when cutting out the image data patches from the image data collected by the imaging unit, and
   the integration unit integrates the output data from the image restoring unit by average or weighted average for overlapped portion when the image data of the adjacent patches are processed by different restorers.

4. The medical imaging device according to claim 1, further comprising an ROI setting unit that sets a region of interest in the image data from the inspection object, wherein
   the image processing unit processes the image data in the region set by the ROI setting unit.

5. The medical imaging device according to claim 1, wherein the image restoring unit comprises a restorer that is not associated with the classifications in addition to the restorers corresponding to the classifications by the classification unit.

6. The medical imaging device according to claim 1, further comprising a storage unit that stores the classification results into a plurality of clusters in advance for a large number of image data by the classification unit, wherein
   the classification unit classifies the image data based on a distance between a centroid of each of the plurality of clusters stored in the storage unit and the image data to be classified.

7. The medical imaging device according to claim 1, wherein
   the imaging unit is an MR imaging unit that measures a magnetic resonance signal from the inspection object, and
   an image generator that converts k-space data including the magnetic resonance signal measured by the MR imaging unit into the image data is further provided, and the image processing unit reconstructs the image using the image data generated by the image generator.

8. The medical imaging device according to claim 7, wherein the plurality of restorers is trained using as the learning data a combination of the image data reconstructed from the k-space data in which all data filling k-space is measurement data and the image data reconstructed from the k-space data measured by thinning.

9. The medical imaging device according to claim 8, wherein the k-space data measured by thinning is data in a circular or polygonal region including a center of the k-space.

10. The medical imaging device according to claim 1, wherein
    the imaging unit is an ultrasonic imaging unit that measures an ultrasonic signal from the inspection object, and
    the image processing unit reconstructs the image data using the image data generated from the ultrasonic signal measured by the ultrasonic imaging unit.

11. The medical imaging device according to claim 1, wherein
    the imaging unit is a CT imaging unit that obtains projection data of X-ray transmitted through the inspection object for each different irradiation angle of the X-ray, and
    an image generator that generates a tomographic image from the projection data obtained by the CT imaging unit is further provided, and the image processing unit reconstructs the image data using the image data generated by the image generator.

12. A medical image processing method for processing original image data obtained by imaging by a medical imaging device and generating image data with improved image quality compared to the original image data, comprising:
    a step (1) of classifying image data of a patch cut out from a correct image according to features of the image data;
    a step (2) of preparing a restorer that is trained using, as learning data, a combination of the correct image and a degraded image obtained by a degradation process for the correct image for each classified cluster;
    a step (3) of classifying the image data to be processed into one of a plurality of clusters obtained in the step (1);
    a step (4) of selecting one or a plurality of restorers from the restorers respectively prepared for the clusters based on results in the step (3);
    a step (5) of inputting the image data to be processed to the restorer selected in the step (4) and obtaining the image data with improved image quality compared to the image data to be processed as an output of the restorer; and
    a step (6) of integrating the output of the plurality of restorers.

13. The medical image processing method according to claim 12, wherein
    the original image data obtained by imaging by the medical imaging device is k-space data obtained by an MRI device, and
    a combination of the image data reconstructed from the k-space data in which all data filling k-space is measurement data and the image data reconstructed from the k-space data measured by thinning is used as the learning data in the step (2).

* * * * *